US006225521B1

(12) United States Patent
Gueret

(10) Patent No.: US 6,225,521 B1
(45) Date of Patent: May 1, 2001

(54) ADHESIVE-MATRIX PATCH

(75) Inventor: Jean-Louis Gueret, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/272,241

(22) Filed: Mar. 19, 1999

(30) Foreign Application Priority Data

Mar. 24, 1998 (FR) .................................................. 98 03589

(51) Int. Cl.⁷ .................................................. A61F 13/00
(52) U.S. Cl. .................................. 602/54; 602/41; 602/43; 602/55; 602/57
(58) Field of Search ........................ 602/41–59; 128/888, 128/889; 206/440, 41; 604/386, 387; 428/221, 261, 317.5, 317.7, 343, 353, 355; 424/443, 447, 448, 449

(56) References Cited

FOREIGN PATENT DOCUMENTS

| 0 309 309 A1 | 3/1989 | (EP) . |
| 0 353 972 A1 | 2/1990 | (EP) . |
| 0 412 869 A1 | 1/1991 | (EP) . |
| 0 413 034 A1 | 2/1991 | (EP) . |
| 0 651 984 A2 | 5/1995 | (EP) . |

*Primary Examiner*—Kim M. Lewis
(74) *Attorney, Agent, or Firm*—Oliff & Berridge, PLC

(57) ABSTRACT

The invention relates to a patch comprising a matrix made of a material having self-adhesive properties to being applied to the skin. The patch includes a permeable structure completely embedded in said matrix close to its surface so as to modify the overall adhesive power thereof.

22 Claims, 1 Drawing Sheet

ADHESIVE-MATRIX PATCH

The present invention relates to a patch for temporary application to the skin to exert a cosmetic and/or pharmaceutical treatment action thereon.

BACKGROUND OF THE INVENTION

Patches are known that comprise a backing sheet coated on one face in a layer forming a reservoir known as a "matrix", containing one or more active substances that are to be diffused into the skin and/or that are to act thereon.

The matrix can be made of a material having adhesive properties, whether intrinsic or otherwise, in which case the patch has an adhesive coating on its surface.

In which case, it is necessary to ensure that the coating does not impede the action of the active substance(s) contained in the matrix.

The invention relates more particularly to a patch in which the matrix is made of a material presenting intrinsic adhesive properties.

Selecting this material raises difficulties, and in particular:
- it must be capable of containing the active substance(s) for acting on the skin;
- its adhesion to the skin must not be too strong, particularly if it is to be applied in repeated manner, since otherwise the region of the body on which the patch is applied will be come irritated, and removing the patch will become painful;
- its adhesion must not be too weak either, since otherwise it will not be able to adhere to the skin if it is moist or if it becomes moist, e.g. because of sweating;
- it must be sufficiently flexible to allow the patch to fit over the shape of the region of the body on which it is applied;
- it must remain on the backing sheet when the patch is removed; and
- finally, it must make it possible to extract the impurities that are to be found on the surface of the skin, in particular sebum or sweat.

In spite of these difficulties, several materials have been proposed for making the matrix, however they are not necessarily suitable for all of the active substances that it might be desirable to incorporate therein.

French patent 2 738 744 or European patent 0 309 309 teach in particular the use of hydrophobic or hyposoluble materials for constituting the matrix.

The hydrosoluble material described in European patent 0 309 309 is relatively impractical in use since it does not present the required adhesive properties prior to application to the skin and it requires the skin to be previously moistened.

European patent application EP-A-0 412 869 describes a composite film having a silicone polymer matrix adjacent to an occlusive matrix. On its side remote from the occlusive layer, the matrix has a reinforcement—constituting screen and a removable protective membrane. The screen reduces the adhesive area of the protective membrane on the matrix.

In such a composite film, the screen locally prevents the matrix from coming into contact with the skin. When the film is withdrawn, the screen runs the risk of leaving a mark on the skin with the mark being all the more pronounced with increasing adhesion of the material constituting the matrix. For a silicone polymer matrix, whose adhesive power (TAC) is relatively low (about 100 g/cm$^2$), this drawback is nevertheless not too troublesome. Finally, the screen prevents a mechanical cleansing action being exerted on the entire area of the skin that is covered by the film.

OBJECTS AND SUMMARY OF THE INVENTION

The present invention seeks to facilitate selecting the material constituting the matrix, but without thereby complicating use of the patch.

This is achieved by the invention by a novel patch comprising a matrix made of a material having self-adhesive properties prior to application to the skin, the patch including a permeable structure completely embedded in said matrix close to its surface so as to modify its overall adhesive power.

Preferably, the permeable structure is hydrophobic.

Also preferably, said permeable structure is constituted by a perforated film, or a solid-fiber cloth that may be woven or non-woven.

When using a hollow fiber cloth, the porosity of the fibers is preferably selected so that they are filled substantially completely by the matrix.

Thus, the permeable structure is not suitable for absorbing moisture present on the skin or the active agent that may be present in the matrix. There is thus no risk of these agents accumulating in the permeable structure, which could delay diffusion thereof into the skin.

Preferably, the permeable structure used is selected so as to present little ability for elongation in the long direction of the patch, so as to make the patch easier to unstick.

Because of the invention, it is possible to control the adhesive properties of the patch on the skin by acting on the nature of the permeable structure used and on the thickness of the matrix situated between the permeable structure and the surface that is to be applied against the skin.

This way of acting on the adhesive properties of the patch make it possible to use a material for making the matrix where, in the absence of said permeable structure, the material would otherwise adhere too strongly to the skin to be suitable for making the looked-for patch.

Thus, by means of the invention, any novel material having intrinsic adhesive properties and that is of interest because of its physical and chemical compatibility with the active substance(s) to be incorporated therewith can be used without any fear of excessively strong adhesion to the skin.

In addition, the permeable structure used makes it possible for the active substance(s) contained in the matrix to diffuse and/or act towards and/or onto the surface of the skin.

Because the permeable structure used for modifying the adhesive power of the matrix is completely embedded in the material constituting the matrix, it is possible to exert mechanical cleansing action over the entire area of the skin covered by the patch, if so desired, since the entire area of the patch that is to come into contact with the skin is adhesive. The risk of leaving a mark on the skin having a pattern corresponding to that of the permeable structure used is also reduced. Finally, when active substances are contained in the matrix, they can exert their action over the entire area of the skin which is in contact with the patch, whereas in European patent application EP-A-0 412 869, the screen applied directly on the skin hinders diffusion of the active agents into the skin, to some extent.

BRIEF DESCRIPTION OF THE DRAWING

Other characteristics and advantages of the present invention appear on reading the following detailed description of non-limiting embodiments of the invention and on examining the accompanying drawing, in which.

MORE DETAILED DESCRIPTION

Figure 1:
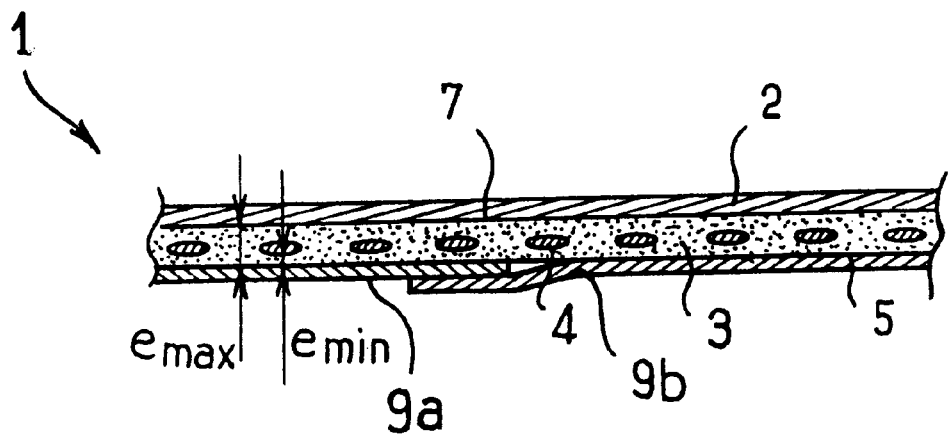
FIG. 1 is a diagrammatic section through a patch constituting a first embodiment of the invention.

FIG. 1 shows a patch 1 constituting a first embodiment of the invention, comprising a backing sheet 2 coated on one face in a matrix 3 made of a material having self-adhesive properties.

The backing sheet 2 may have been subjected to corona treatment in order to improve the adhesion of the matrix.

A perforated structure constituted in this case by a polyamide net 4 is embedded in the matrix 3 close to its surface 5 that is to come into contact with the skin.

The perforated structure used is advantageously hydrophobic and has no particular ability at absorbing moisture and/or the active substances that may be contained in the matrix 3. Thus, it is not liable to swell with water or with active substances while the patch is in use, since that could reduce adhesion of the patch and/or delay diffusion of said substances into the skin.

It will be observed that the presence of the net 4 close to the surface of the patch that is to come into contact with the skin has no effect on the adhesion of the matrix to the backing sheet.

In the example described, the total thickness $e_{max}$ of the matrix 3 is constant, e.g. lying in the range 0.1 mm to 3 mm.

The net 4 is situated at a distance $e_{min}$ from the surface 5, and its strands co-operate therewith to define zones of reduced thickness, and thus of reduced adhesion for the material constituting the matrix 3.

Preferably, the ratio $e_{min}/e_{max}$ is less than or equal to 1/10.

For given thickness of the matrix 3, the presence of the net 4 within the matrix 3 gives rise to local variations in the adhesion of the patch 1 on the skin, and to overall adhesion of the patch 1 that is less than that which it would have been if the net 4 were omitted.

It is possible to act on the ratio $e_{min}/e_{max}$ to adapt the adhesion of the patch 1 as a function of the sensitivity of the zone on which it is to be applied, and where appropriate to the active substance(s) incorporated within the matrix 3.

The backing sheet 2 is made of a flexible material, e.g. polyester, polyethylene, or polypropylene, or any other appropriate material, optionally an occlusive material.

It can be advantageous to metallize the backing sheet 2 so as to reflect thermal radiation from the body back towards the surface of the skin, and to enable the matrix 3 to be raised quickly to the temperature of the user, which can have the consequence of increasing the adhesion of the patch and/or of enhancing diffusion and/or the action of the active substance(s) optionally contained therein.

The thickness of the metallized backing sheet can lie, for example, in the range 20 μm to 120 μm.

In a variant, the backing sheet can be constituted by a metal foil.

The patch may also have a layer suitable for picking up thermal radiation from outside radiation.

It may also be advantageous to color the matrix 3 and/or the net 4 and/or the backing sheet 2 using a dark color so that after the user has removed the patch 1, the user can, by contrast, observe the quantity and/or the nature of the impurities removed. The user can then determine whether further application is required and also, where appropriate, whether the frequency and/or the nature of the treatment need to be modified. For example, it is possible to incorporate in the matrix violet pigments as sold by RDF Chimie under the reference DC violet 2K7014.

The material used for making the matrix 3 advantageously includes one or more acrylic or vinyl polymers, polyurethane, EPDM, or an elastomer whose adhesion (measured parallel to the surfaces in contact) preferably lies in the range 300 $g/cm^2$ to 800 $g/cm^2$.

For example, an acrylic adhesive is used in a solvent base (ethyl acetate hexane ethanol) that is self-curing, sensitive to pressure, having initial adhesion of about 100 $g/cm^2$, and adhesive power (TAC) after it has been in place for a sufficient length of time of about 300 $g/cm^2$. One such adhesive is sold by MAPEI under the name AGXL.

The use of a metallized backing sheet makes it possible to reduce the time required for the adhesive to reach adhesive power close to its maximum adhesive power, by concentrating heat on the skin/matrix interface.

Because of the presence of the net 4, the adhesive power of the material used for making the matrix 3 can be reduced to 50% or even less, e.g. from 600 $g/cm^2$ without a net to 200 $g/cm^2$ or even 150 $g/cm^2$ in the presence of the net.

Advantageously, the matrix 3 has one or more active substances that have an effect on the skin, e.g. such as, anti-oxidants, free radical scavengers, moisturizers, depigmenting agents, liporegulators, anti-acne agents, anti-dandruff agents, anti-aging agents, softeners, anti-wrinkle agents, keratolytic agents, anti-inflammatory agents, fresheners, healing agents, vascular protectors, antibacterial agents, antifungal agents, antiperspirants, deodorants, skin conditioners, anesthetics, immunomodulators and nourishing agents, moisture absorbers (cotton, polyacrylate), and sebum absorbers (Orgasol).

Preferably, the patch 1 is covered, prior to use, with a removable protective membrane overlying its surface that is to come into contact with the skin.

This protective membrane preferably has two portions 9a and 9b that overlap in the middle region of the patch so as to enable the user to remove them without the fingers touching the matrix 3, and thus without causing it to lose its adhesive power.

The patch of the invention can be manufactured by coating the net 4 with the material that is to constitute the matrix 3 while soaked in one or more solvents, thereafter bringing the assembly into contact with a temporary backing that withstands temperature, and then pressing the entire assembly in an oven for evaporating the above-specified solvent(s).

On leaving the oven, the temporary backing is separated from the matrix 3 which has been secured to the net 4, and the matrix and the net are applied together to the face 7 of the backing sheet 2, the assembly then being calendared.

It should be understood that the invention is not limited solely to using a net 4 as described for making the perforated structure. It is also possible to use any other permeable structure, perforated film, or woven or non-woven cloth, for example.

Figure 2:
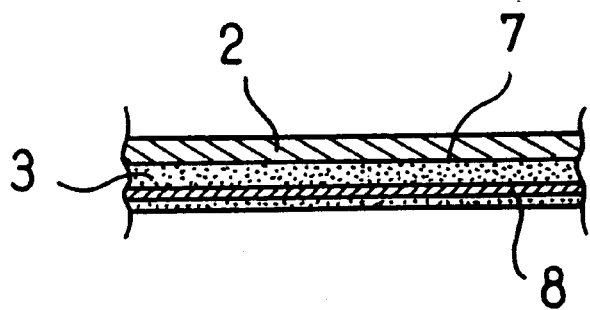
FIG. 2 is a diagrammatic section through a patch constituting an embodiment of the invention.

FIG. 2 shows a patch constituting a second embodiment of the invention.

This patch differs from that described with reference to FIG. 1 in that the permeable structure used is not a net but a non-woven cloth 8 of polyethylene fibers through which, where appropriate, one or more substances contained in the matrix can diffuse.

The non-woven cloth 8 is positioned within the matrix 3 so as to modify the overall adhesive power thereof and thus obtain the desired adhesion.

The overall adhesive power of the patch can also be modified, where appropriate, by having relief present in the surface of the matrix.

Such relief can be implemented by using an embossed protective membrane which leaves the desired relief on the matrix after it has been removed.

The patch 1 is preferably presented to the user in a pre-cutout state, so as to fit the shape of the region of the body that is to be treated, with its size lying, for example, in the range 1 cm$^2$ to 30 cm$^2$.

The patch is preferably packaged in a protective sachet made up of two sheets of a watertight composite of paper and plastics material film, e.g. made of polypropylene, where the paper is coated in an adhesive that operates cold, with the sheets being stuck together around the patch by putting adhesive-coated faces into contact.

Such packaging serves to protect the patch from air and to improve its conditions of conservation.

The length of time the patch is applied to the skin can lie in the range 30 seconds to 5 minutes, for example, and preferably lies in the range 1 minute to 5 minutes.

What is claimed is:

1. A patch comprising a matrix made of a material having self-adhesive properties prior to application to the skin, the patch including a permeable structure completely embedded in said matrix close to its surface so as to modify its overall adhesive power.

2. A patch according to claim 1, wherein said permeable structure produces local variations in the adhesive power of the matrix and is preferably constituted by a net.

3. A patch according to claim 1, wherein the permeable structure is constituted by a non-woven cloth.

4. A patch according to claim 1, wherein, in said matrix, the patch includes at least one active substance having an effect on the skin.

5. A patch according to claim 4, wherein the at least one active substance is selected from the group consisting of anti-oxidants, free radical scavengers, moisturizers, depigmenting agents, liporegulators, anti-acne agents, anti-dandruff agents, anti-aging agents, softeners, anti-wrinkle agents, keratolytic agents, anti-inflammatory agents, fresheners, healing agents, vascular protectors, antibacterial agents, antifungal agents, antiperspirants, deodorants, skin conditioners, anesthetics, immunomodulators and nourishing agents, moisture absorbers, and sebum absorbers.

6. A patch according to claim 1, wherein said matrix comprises one or more acrylic or vinyl polymers.

7. A patch according to claim 1, wherein said permeable structure is of a dark color.

8. A patch according to claim 1, wherein said matrix has a dark color.

9. A patch according to claim 1, wherein said matrix is carried by a backing sheet of dark color, at least on its face facing towards said matrix.

10. A patch according to claim 1, wherein said matrix is carried by a metal foil or a metallized backing sheet.

11. A patch according to claim 10, wherein the thickness of the metallized backing sheet is in a range of 20 $\mu$m to 120 $\mu$m.

12. A patch according to claim 1, wherein its size lies in the range 1 cm$^2$ to 30 cm$^2$, and wherein it is pre-cutout so as to match the shape of the region of the body to be treated.

13. A patch according to claim 1, wherein the ratio of the thickness of the material constituting said matrix between the permeable structure and the surface that is to be pressed against the skin over the total thickness of said matrix is less than or equal to 1/10.

14. A patch according to claim 1, wherein the material used for making the matrix has adhesion lying in the range 300 g/cm$^2$ to 600 g/cm$^2$.

15. A patch according to claim 1, wherein the matrix is coated prior to use with a protective membrane comprising two portions that overlap in the middle region of the patch.

16. A patch according to claim 1, including a layer suitable for picking up heat energy from external radiation.

17. A patch according to claim 1, packaged in a protective sachet made up of two sheets of a leakproof laminate of paper and plastics material film, the paper being coated in an adhesive that operates cold, the sheets being sealed around the patch by putting their faces that are coated in adhesive into contact.

18. A method of using the patch as defined in claim 1, comprising: leaving the patch is left for a period of application that lies in a range of 30 seconds to 5 minutes.

19. A patch according to claim 1, wherein the matrix has a thickness from about 0.1 mm to 3.0 mm.

20. A patch comprising a backing sheet carrying a matrix made of a material having self-adhesive properties prior to application to the skin, the patch including a permeable structure completely embedded in said matrix close to the surface of the matrix to be applied to the skin so as to modify the overall adhesive power of said matrix, wherein said permeable structure is spaced from said backing sheet.

21. A patch comprising a backing sheet carrying a matrix made of a material having self-adhesive properties prior to application to the skin, the patch including a permeable structure completely embedded in said matrix close to the surface of the matrix to be applied to the skin so as to modify the overall adhesive power of said matrix, wherein said permeable structure is spaced from said backing sheet and wherein said matrix comprises one or more acrylic or vinyl polymers.

22. A patch comprising a backing sheet carrying a matrix made of a material having self-adhesive properties prior to application to the skin, the patch comprising a permeable structure completely embedded in said matrix, said permeable structure being at a distance from the surface of the matrix to be applied to the skin, which is less than the distance separating said permeable structure from the backing sheet, so as to modify the overall adhesive power of said matrix.

\* \* \* \* \*